United States Patent [19]

Guillou et al.

[11] Patent Number: Plant 7,358

[45] Date of Patent: Oct. 16, 1990

[54] VARIETY OF GERANIUM NAMED NICOLE

[75] Inventors: Jacques Guillou; Bernard Guillou; Maurice Guillou, all of Saint-Malo, France

[73] Assignee: Etablissement Guillou Freres Jacques, Bernard et Maurice, France

[21] Appl. No.: 359,734

[22] Filed: May 31, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Webb, Burden, Ziesenheim & Webb

[57] ABSTRACT

A new variety of Ivy Geranium having proven to be superior in plant habit, bloom color and heat tolerance than Galilee, the current market Ivy Geranium now available. The new variety also has smaller darker leaves and earlier bloom than Galilee. The medium green foliage is accented with a darker green zone. The clear, clean pink has less tendency to burn or shatter. This combination creates a full, beautiful hanging basket.

1 Drawing Sheet

BACKGROUND OF THE NEW PLANT

The present invention comprises a new and distinct cultivar of *Pelargonium*×*peltatum* known by the varietal name Nicole (Oglevee Ltd. No. 7045, French No. 508 Guicerdan). The new variety was discovered in a selective breeding program by Messrs. Jacques, Maurice and Bernard Guillou. The new variety is a selection from the crossing of Solidor 85×Bouvet 14. The new variety has a more zoned foliage, is more floriferous and keeps better than its parentage.

The new cultivar was discovered in 1985 at 55 rue Godard, 35400 Saint-Malo, France, was first asexually reproduced by cuttings during 1986 at Saint-Malo, France, and more recently has been repeatedly asexually reproduced by cuttings at Oglevee Ltd. in Connellsville, Pa. It has been found to retain its distinct propagation through successive characteristics.

The new cultivar, when grown in a glass greenhouse in Connellsville, Pa., using full light, 60° F. night temperature, 68° F. day temperature, 71° F. vent temperature, and grown in a soilless media with constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted on Aug. 1, 1988 and flowered on Sept. 15, 1988. Three 10 cm pots were potted into a 26 cm hanging basket and the plant was maintained until Feb. 27, 1989 when the color readings were taken. The plant histories were taken of plants blossomed under full light in a greenhouse and color readings were taken indoors under 200–220 foot candles of cool white florescent light. Color references are primarily to The R.H.S.

Colour Chart of The Royal Horticultural Society of London.

THE PLANT

Classification:

*Botanical.*—*Pelargonium*×*peltatum.*

*Commercial.*—Ivy Geranium (#7045) Nicole.

Form: Cascading mound habit.

Height: 17 cm above media surface.

Growth: Free branching, upright mound with cascading side growth, free and early flowering.

Strength: Holds an upright mound shape while allowing outer branches to cascade over the sides of the pot.

Foliage: Stalked leaf attachment; zone present.

Leaves:

*Size.*—5.5–8 cm across; fully expanded leaf.

*Shape.*—Reniform, cordate base.

*Margin.*—Pedately lobed.

*Texture.*—Leathery; slightly reflective.

*Color.*—Top: Green group 137A; Zone: Greyed-purple group 183A; Bottom: Green group 137C.

*Ribs and veins.*—Palmated venation; Color: Green group 137C.

Petioles: 4–7 cm in length.

*Color.*—Yellow-green group 146B.

Stem:

*Color.*—Yellow-green group 146A.

*Internodes.*—1.5–3.5 cm in length.

THE BUD

Shape: Semi-hemispherical cluster, 5–9 florets per umbel, peduncle has a bent neck until maturity when it straightens out.

Size: 2.5–3 cm across.

INFLORESCENCE

Blooming habit: Continuous; upright; hemispherical; some shattering present as open bloom matures.

Size: 7–7.5 cm when full open.

Borne: Florets on pedicel; pedicel on peduncle; umbel 4–6 cm above foliage canopy.

Florets:

*Form.*—Flat to slightly cupped.

*Color.*—Top: Red-purple group 62A with a touch of Red group 38D on each petal close to center of floret. Venation on upper 3–4 petals: Red-purple group 61B with a blotch of Red-purple group 62C between veins. Bottom: Red-purple group 62C.

*Petals.*—13–15 in number, separate, not united; margin entire.

*Floret size.*—4.5–5 cm across.

*Texture and appearance.*—Smooth; appearance from a distance is a clear medium pink with upper petals with burgundy and white markings.

Petaloids:

*Quantity.*—Zero to three.

*Shape.*—Elongated, twisted, some with anther attached.

*Color.*—Red-purple group 62A.

Pedicel: 1.5–3 cm in length.

*Color.*—Yellow-green group 146B.

Peduncle: 8.5–12.5 cm in length.

*Color.*—Yellow-green group 146B. Arises from the node opposite leaf petiole.

Disease resistance: Not known.

Lasting Quality: Compared to current ivies this variety is more tolerant of heat and shatters less.

REPRODUCTIVE ORGANS

Stamens:

*Anthers.*—2–3 mm in length.

*Filaments.*—5–11 mm in length; irregular shape; white to light pink in color.

*Pollen.*—Golden brown—Greyed-orange group 171A.

Pistils:

*Number.*—One; 5 or 6 parted stigma.

*Length.*—10–12 mm.

*Stigma.*—5 or 6 parted.

*Style.*—4–5 mm in length; white.

Ovaries: Very pubescent; superior; pale green; 4–5 mm in length, 1–2 mm across.

Fruit: None observed.

GENERAL CHARACTERISTICS

This variety of Ivy Geranium has proven to be superior in plant habit, bloom color and heat tolerance than Galilee, the current market ivy geranium now available.

The medium green foliage is accented with a darker green zone. The clear, clean pink has less tendency to burn or shatter. The combination creates a full, beautiful hanging basket.

When compared to the variety Galilee, Nicole is more compact, more pronounced zone in leaf, more floriferous, earlier bloomer and has smaller darker leaves.

We claim:

1. A new and distinct variety of Ivy Geranium plant as shown and described herein, and characterized by less tendency to burn or shatter, smaller darker leaves, earlier bloom, a superior compact plant habit, a clean pink bloom color, a dark green leaf zone and better heat tolerance as compared with Galilee.

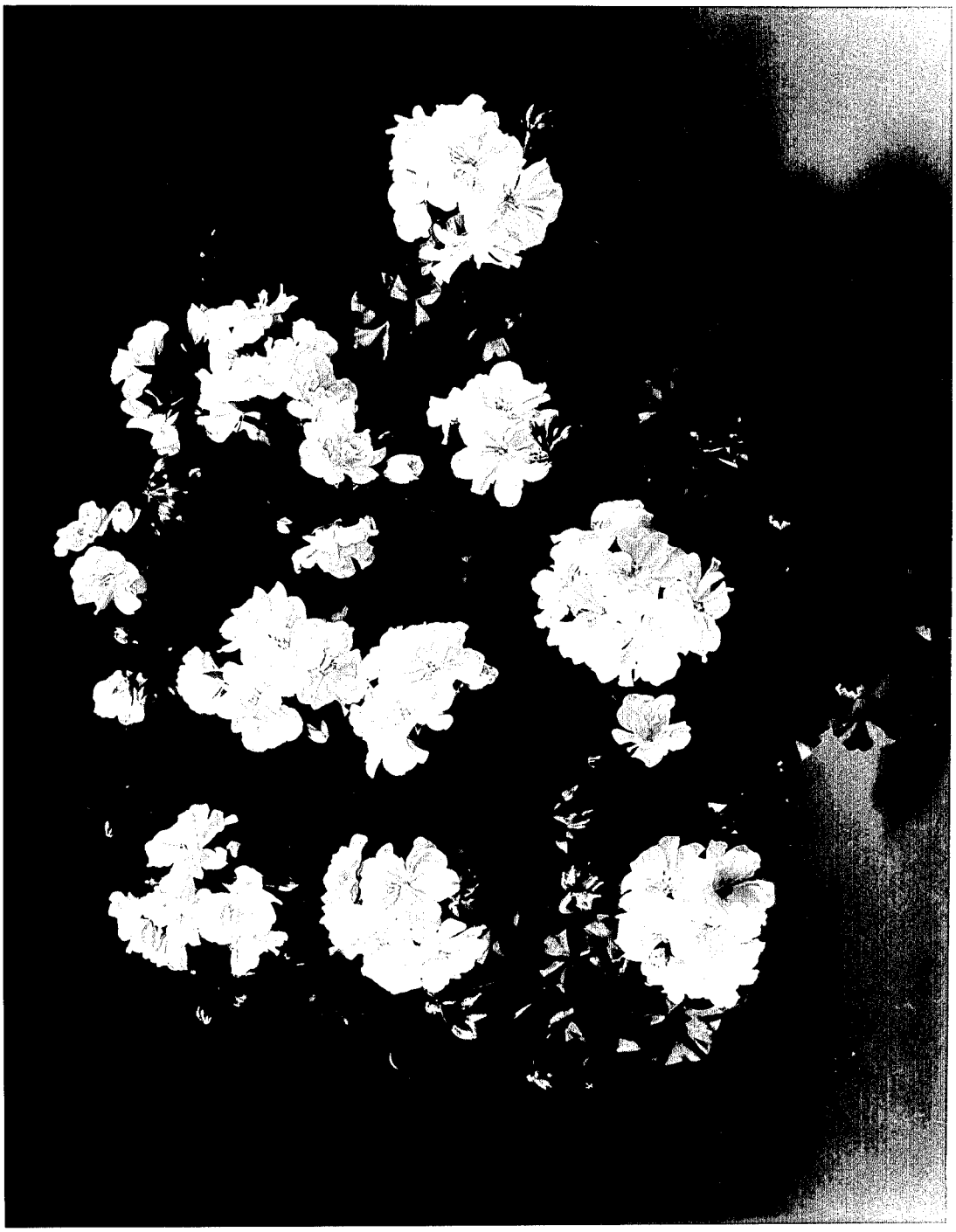

* * * * *